(12) United States Patent
Grandeury et al.

(10) Patent No.: US 10,934,273 B2
(45) Date of Patent: Mar. 2, 2021

(54) CRYSTALLINE FORMS OF 4-(2-((1R,2R)-2-HYDROXYCYCLO-HEXYLAMINO)BENZOTHIAZOL-6-YLOXY)-N-METHYLPICOLINAMIDE

(71) Applicant: Novartis AG, Basel (CH)

(72) Inventors: Arnaud Grandeury, Helfrantzkirch (FR); Liladhar Murlidhar Waykole, Succasunna, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/341,124

(22) PCT Filed: Oct. 13, 2017

(86) PCT No.: PCT/IB2017/056379
§ 371 (c)(1),
(2) Date: Apr. 11, 2019

(87) PCT Pub. No.: WO2018/069892
PCT Pub. Date: Apr. 19, 2018

(65) Prior Publication Data
US 2020/0190057 A1     Jun. 18, 2020

Related U.S. Application Data

(60) Provisional application No. 62/408,358, filed on Oct. 14, 2016.

(51) Int. Cl.
*C07D 401/12*     (2006.01)
*A61P 35/00*      (2006.01)

(52) U.S. Cl.
CPC ............ *C07D 401/12* (2013.01); *A61P 35/00* (2018.01); *C07B 2200/13* (2013.01)

(58) Field of Classification Search
CPC .. C07B 2200/13; C07D 417/12; C07D 401/12
See application file for complete search history.

(56) References Cited

U.S. PATENT DOCUMENTS

2008/0405528     2/2008 Sutton

FOREIGN PATENT DOCUMENTS

WO     WO2007/121484 A2     10/2007

OTHER PUBLICATIONS

H Brittain, ed. Polymorphism in Pharmaceutical Solids (1999) p. 235-238.*
Caira Ed—Montchamp Jean-Luc, "Crystalline Polymorphism of Organic Compounds", Topics in Current Chemistry, Springer, Berlin, DE, vol. 198, pp. 163-208, 1998.
Serajuddin et al., "Salt formation to improve drug solubility", Advanced Drug Delivery Reviews, Elsevier, Amsterdam, NL, vol . 59, No. 7, pp. 603-616, Aug. 24, 2007 (Aug. 24, 2007).
(Continued)

*Primary Examiner* — Valerie Rodriguez-Garcia
(74) *Attorney, Agent, or Firm* — Michelle Han (57) ABSTRACT

This application relates to various crystalline forms of 4-(2-((1R,2R)-2-hydroxycyclohexylamino)benzothiazol-6-yloxy)-N-methylpicolinamide hydrochloride salts as well as compositions and methods of using the same. In some embodiments the crystalline forms also contain water ("hydrates"). These materials are useful in the treatment of various diseases, including glioblastoma multiforme, breast cancer, pancreatic cancer and other solid tumors.

14 Claims, 3 Drawing Sheets

(56) References Cited

OTHER PUBLICATIONS

John F Bauer, "Pharmaceutical Solids—The Amorphous Phase", Journal of Validation Technology, vol. 15, No. 3, pp. 63-68, 2009.
Brittain, H.G. in "Polymorphism in Pharmaceutical Solids", 2nd Edition, Marcel Dekker, Inc., New York, Edited by Brittain, (2009).
Berge, Stephen M "Pharmaceutical Salts", Journal of Pharmaceutical Sciences, vol. 66, No. 1, pp. 1-19, Jan. 1977.
Bastin, Richard J et al. "Salt selection and Optimization Procedures for Pharmaceutical New Chemical Entities" Organic Process Research & Development, 2000, vol. 4, p. 427-435.

\* cited by examiner

CRYSTALLINE FORMS OF 4-(2-((1R,2R)-2-HYDROXYCYCLO-HEXYLAMINO)BENZOTHIAZOL-6-YLOXY)-N-METHYLPICOLINAMIDE

RELATED APPLICATIONS

This application claims priority to, and the benefit of, U.S. provisional application No. 62/408,358, filed Oct. 14, 2016, the entire content of which is incorporated herein by reference in its entirety.

FIELD OF INVENTION

The present disclosure generally relates to crystalline forms of 4-(2-((1R,2R)-2-hydroxycyclohexylamino)benzothiazol-6-yloxy)-N-methylpicolinamide. The present disclosure also generally relates to a pharmaceutical composition comprising the crystalline forms, as well of methods of using the crystalline forms in the treatment of particular cancers, and methods for obtaining such crystalline forms.

BACKGROUND 4-(2-((1R,2R)-2-hydroxycyclohexylamino)benzothiazol-6-yloxy)-N-methylpicolinamide was first disclosed in WO2007/121484, filed Apr. 18, 2007, which is incorporated by reference in its entirety, is a CSF-1R kinase inhibitor having the structure of Formula I:

Formula I

The compound of Formula I is useful in the treatment of various disease states associated with the activation of non-neoplastic cells such as fibroblasts, endothelial cells and macrophages. As such, the compound of Formula I is therefore useful in the treatment of certain cancers, including, for example, glioblastoma multiforme, breast cancer, pancreatic cancer and other solid tumors.

It is well known that the solid state form of the active pharmaceutical ingredient (API) of a particular drug is often an important determinant of the drug's ease of preparation, hygroscopicity, stability, solubility, storage stability, ease of formulation, rate of dissolution in gastrointestinal fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc. are deemed to be critical. In other situations, a different form may be preferred for greater dissolution rate and/or superior bioavailability. It is not yet possible to predict whether a particular compound or salt of a compound will form polymorphs, whether any such polymorphs will be suitable for commercial use in a therapeutic composition, or which polymorphs will display such desirable properties.

SUMMARY

The present disclosure provides crystalline forms of 4-(2-((1R,2R)-2-hydroxycyclohexylamino)benzothiazol-6-yloxy)-N-methylpicolinamide hydrochloride salts. In some embodiments, the hydrochloride salts further include water (referred to herein as hydrates). Embodiments of these crystalline forms include those forms designated herein as Form A and Form B. The names used herein to identify a specific form, e.g. "Form A" etc., should not be considered limiting with respect to any other substance possessing similar or identical physical and chemical characteristics, but rather it should be understood that these designations are mere identifiers that should be interpreted according to the characterization information also presented herein.

Figure 1:
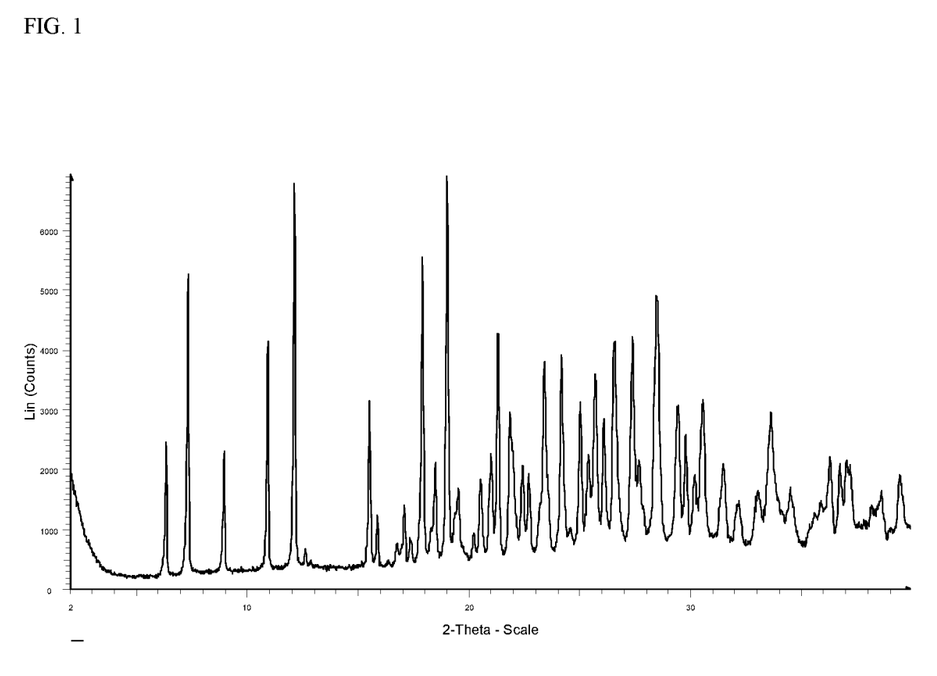
FIG. 1 provides an illustrative XRPD spectrum for the di-hydrochloride (HCl) monohydrate salt of the compound of Formula I, designated herein as Form A, showing degrees 2θ (2-theta) on the X-axis and relative intensity on the Y-axis.
Figure 2:
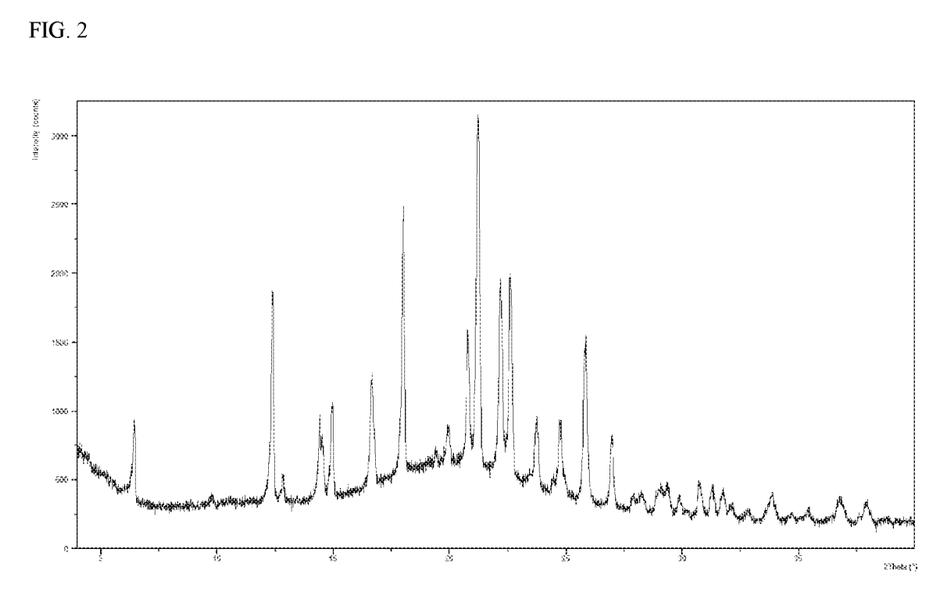
FIG. 2 provides an illustrative XRPD spectrum for the mono-hydrochloride (HCl) salt of the compound of Formula I, designated herein as Form B, showing degrees 2θ (2-theta) on the X-axis and relative intensity on the Y-axis.

More detailed listings of the XRPD peaks for each of Forms A and B are set forth in Tables 1 and 2 below, in which the % relative intensity ($I/I_0 \times 100$) is also provided. It should be understood that in the X-ray powder diffraction spectra or pattern that there is inherent variability in the values measured in degrees 2θ (°2θ) as a result of, for example, instrumental variation (including differences between instruments). As such, it should be understood that there is a variability of up to ±0.2 °2θ in XRPD peak measurements and yet such peak values would still be considered to be representative of a particular solid state form of the crystalline materials described herein. It should also be understood that other measured values from XRPD experiments and Karl Fisher analysis, such as relative intensity and water content, can vary as a result of, for example, sample preparation and/or storage and/or environmental conditions, and yet the measured values will still be considered to be representative of a particular solid state form of the crystalline materials described herein.

DETAILED DESCRIPTION OF THE DISCLOSURE

The present disclosure relates to crystalline forms of various hydrochloride salts of 4-(2-((1R,2R)-2-hydroxycyclohexylamino)benzothiazol-6-yloxy)-N-methylpicolinamide (the compound of Formula I), which are described and characterized herein.

In one embodiment, the present disclosure provides a crystalline form of the di-hydrochloride monohydrate salt of 4-(2-((1R,2R)-2-hydroxycyclohexylamino)benzothiazol-6-yloxy)-N-methylpicolinamide (Form A) having an X-ray powder diffraction (XRPD) pattern comprising a representative peak, in terms of °2θ, at 12.1±0.2 °2θ. In another embodiment, the XRPD pattern further comprises one or more additional representative peaks chosen from 7.3±0.2 °2θ, 10.9±0.2 °2θ, and 17.9±0.2 °2θ. In another embodiment, the XRPD pattern further comprises one or more additional representative peaks chosen from 6.3±0.2 °2θ, 7.3±0.2 °2θ, 10.9±0.2 °2θ, 17.9±0.2 °2θ and 19.0±0.2 °2θ. Accordingly, the XRPD pattern for the crystalline form of the di-hydrochloride monohydrate salt of the compound of Formula I may comprise one, two, three, or four representative peaks. In another embodiment, the crystalline form of the di-hydrochloride monohydrate salt of the compound of Formula I has an XRPD pattern that may further include one or more additional representative peaks chosen from 8.9±0.2 °2θ, 21.2±0.2 °2θ and 24.2±0.2 °2θ. Thus, the XRPD pattern for the crystalline form of the di-hydrochloride monohydrate salt of the compound of Formula I may comprise one, two, three, four, five or six representative peaks. In yet another embodiment, a crystalline form of the di-hydrochloride monohydrate salt of the compound of Formula I has an XRPD pattern substantially as shown in FIG. 1. It should be understood that the water content of Form A can be in the range of about 3.2% to about 4.0% and still be considered to be a monohydrate having the XRPD pattern comprising the one, two, three, four, five or six representative peaks described above. The theoretical water content for Form A is 3.68%.

Figure 3:
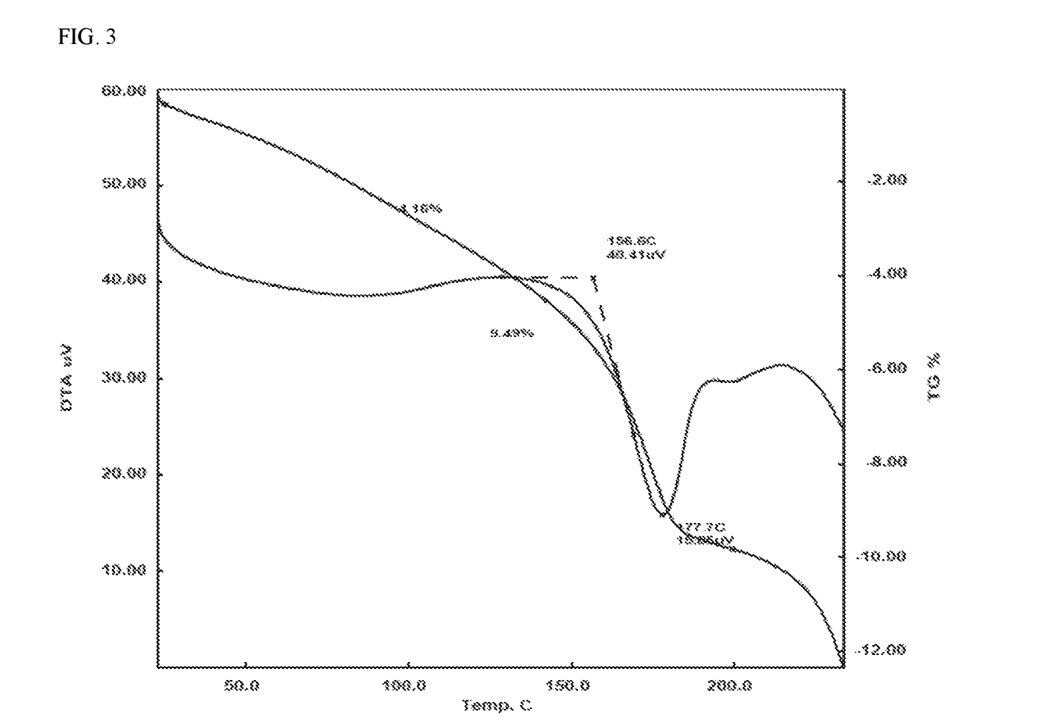
FIG. 3 provides an illustrative TG/DTA (thermogravimetry and differential thermal analysis) trace for the di-hydrochloride (HCl) monohydrate salt of the compound of Formula I, designated herein as Form A.

The crystalline form of the di-hydrochloride monohydrate salt of 4-(2-((1R,2R)-2-hydroxycyclohexylamino)benzothiazol-6-yloxy)-N-methylpicolinamide may be characterized thermally. In one embodiment, a crystalline form of the di-hydrochloride monohydrate salt of the compound of Formula I has a differential thermogravimetric profile comprising an endotherm starting at about 156.6° C. In another embodiment, a crystalline form of the di-hydrochloride monohydrate salt of the compound of Formula I has a TG/DTA profile that is substantially as shown in FIG. 3. It should be understood that hydrated forms may yield different thermograms (in terms of peak shape and profile) depending on instrument parameters, thus the same material may have thermograms that look substantially different from each other when the data is generated on two different instruments.

In another embodiment, the present disclosure provides a crystalline form of a mono-hydrochloride salt of 4-(2-((1R,2R)-2-hydroxycyclohexylamino)benzothiazol-6-yloxy)-N-methylpicolinamide (Form B) having an X-ray powder diffraction (XRPD) pattern comprising a representative peak, in terms of °2θ, at 14.4±0.2 °2θ. In another embodiment, the XRPD pattern further comprises one or more additional representative peaks chosen from 6.4±0.2 °2θ, 12.4±0.2 °2θ, and 15.0±0.2 °2θ. Accordingly, the XRPD pattern for the crystalline form of the mono-hydrochloride salt of the compound of Formula I may comprise one, two, three, or four representative peaks. In another embodiment, the crystalline form of the mono-hydrochloride salt of the compound of Formula I has an XRPD pattern that may further include one or more additional representative peaks chosen from 18.0±0.2 °2θ and 21.2±0.2 °2θ. Thus, the XRPD pattern for the crystalline form of the mono-hydrochloride salt of the compound of Formula I may comprise one, two, three, four, five or six representative peaks. In yet another embodiment, a crystalline form of the mono-hydrochloride salt of the compound of Formula I has an XRPD pattern substantially as shown in FIG. 2.

As used herein, the terms "about" and "substantially" indicate with respect to features such as endotherms, exotherms, baseline shifts, etc., that their values can vary ±2° C. For differential scanning calorimetry (DSC), variation in the temperatures observed will depend upon the rate of temperature change as well as sample preparation technique and the particular instrument employed. Thus, the endotherm/melting point values reported herein relating to TG/DTA thermograms can vary ±4° C. (and still be considered to be characteristic of the particular crystalline form of 4-(2-((1R, 2R)-2-hydroxycyclohexylamino)benzothiazol-6-yloxy)-N-methylpicolinamide referenced). When used in the context of other features, such as, for example, percent by weight (% by weight) the term "about" indicates a variance of ±5%.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Alternatively, solvates may occur as dimers or oligomers comprising more than one molecule or within the crystalline lattice structure.

As used herein "amorphous" refers to a solid form of a molecule, atom, and/or ions that is not crystalline. An amorphous solid does not display a definitive X-ray diffraction pattern.

As used herein, "substantially phase pure," when used in reference to any crystalline form of the compound of Formula I, means a compound having a phase purity of greater than about 90% by weight, including greater than about 90, 91, 92, 93, 94, 95, 96, 97, 98, and about 99% by weight, and also including equal to about 100% by weight of the compound of Formula I, based on the weight of the compound on an anhydrous basis. The term "phase pure" or "phase purity" herein refers to phase homogeneity with respect to a particular solid state form of the compound of Formula I and does not necessarily imply a high degree of chemical purity absent an express statement to that effect. In certain embodiments, the term "substantially phase pure" with reference to a particular polymorphic form means that the polymorphic form includes less than 10%, preferably less than 5%, more preferably less than 3%, most preferably less than 1% by weight of any other physical forms of the compound. For example, "substantially phase pure Form A" refers to less than 10% by weight of any other physical forms of the compound of Formula (I) such as amorphous forms and From B. Phase purity may be determined according to methods known in the art, for example, using XRPD to do quantitative phase analysis using one or more approaches known in the art, for example, via an external standard method, direct comparisons of line (peak) characteristics which attributed to different phases in a particular spectra, or via an internal standard method. However XRPD quantification of phase purity can be complicated by the presence of amorphous material. Accordingly, other methods that may be useful for determining phase purity include, for example, solid state NMR spectroscopy, Raman and/or infrared spectroscopy.

As used herein, "substantially chemically pure" when used in reference to any crystalline form of the compound of Formula I, means a compound having a chemical purity greater than about 90% by weight, including greater than about 90, 91, 92, 93, 94, 95, 96, 97, 98, and about 99% by weight, and also including equal to about 100% by weight of the compound of Formula I, based on the weight of the salt (on an anhydrous basis). The remaining material generally comprises other compounds, such as for example, other stereoisomers of the compound of Formula I, reaction impurities, starting materials, reagents, side products, and/or other processing impurities arising from the preparation and/or isolation and/or purification of the particular crystalline form. For example, a crystalline form of the compound of Formula I may be deemed substantially chemically pure if it has been determined to have a chemical purity of greater than about 90% by weight, as measured by standard and generally accepted methods known in the art, where the remaining less than about 10% by weight constitutes other materials such as other stereoisomers of the compound of Formula I, reaction impurities, starting materials, reagents, side products, and/or processing impurities. Chemical purity may be determined according to methods known in the art, for example, high performance liquid chromatography (HPLC), LC-MS (liquid chromatography—mass spectrometry), nuclear magnetic resonance (NMR) spectroscopy, or infrared spectroscopy.

The term "a therapeutically effective amount" of a compound disclosed herein refers to an amount of the compound that will elicit a biological or medical response in a subject, for example, reduction or inhibition of an enzyme or a protein activity, or ameliorate symptoms, alleviate conditions, or slow or delay disease progression, etc. In one non-limiting embodiment, the term "a therapeutically effective amount" refers to the amount of the compound that, when administered to a subject, is effective to (1) at least partially alleviating, inhibiting, and/or ameliorating a condition, or a disorder or a disease (i) mediated by CSF-1R, or (ii) associated with CSF-1R activity, or (iii) characterized by activity (normal or abnormal) of CSF-1R; or (2) reducing or inhibiting the activity of CSF-1R; or (3) reducing or inhibiting the expression of CSF-1R. In another non-limiting embodiment, the term "a therapeutically effective amount" refers to the amount of the compound that, when administered to a cell, or a tissue, or a non-cellular biological material, or a medium, is effective to at least partially reducing or inhibiting the activity of CSF-1R; or at least partially reducing or inhibiting the expression of CSF-1R.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or disorder or at least one of the clinical symptoms thereof). In another embodiment "treat", "treating" or "treatment" refers to alleviating or ameliorating at least one physical parameter associated with the disease or condition including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to delaying the onset or development or progression of the disease or disorder.

The crystalline forms of 4-(2-((1R,2R)-2-hydroxycyclohexylamino)benzothiazol-6-yloxy)-N-methylpicolinamide described herein are useful in the treatment of a variety of cancers, including, for example breast cancer (more specifically, triple negative breast cancer), pancreatic cancer and brain cancers (such as, for example, glioma and glioblastoma multiforme). In some embodiments, the crystalline forms of 4-(2-((1R,2R)-2-hydroxycyclohexylamino)benzothiazol-6-yloxy)-N-methylpicolinamide described herein are used as single agents or in combination with well-known standard of care (SOC) therapies for the disease or condition to be treated. In other embodiments, the crystalline forms of 4-(2-((1R,2R)-2-hydroxycyclohexylamino)benzothiazol-6-yloxy)-N-methylpicolinamide described herein may be used in conjunction with other treatment modalities such as, for example, surgery or radiation therapy.

In some embodiments the crystalline forms of 4-(2-((1R,2R)-2-hydroxycyclohexylamino)benzothiazol-6-yloxy)-N-methylpicolinamide described herein can be used alone or they can be formulated into a pharmaceutical composition that also contains at least one pharmaceutically acceptable excipient, and often contains at least two or more pharmaceutically acceptable excipients. Some suitable excipients are disclosed herein. Other excipients may be used that are known in the art without departing from the intent and scope of the present application.

In some embodiments, the present invention utilizes a pharmaceutical composition comprising a crystalline form of the present invention and a pharmaceutically acceptable excipient. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, carriers or buffering agents, as well as adjuvants, such as solvents, preservatives, stabilizers, wetting agents, emulsifiers and bulking agents, etc.

Typically, the pharmaceutical compositions are tablets or capsules comprising the active ingredient together with at least one excipient, such as:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired;

d) carriers such as an aqueous vehicle containing a co-solvating material such as captisol, PEG, glycerin, cyclodextrin, or the like;

e) disintegrants, e.g., starches, agar, alginic acid or its sodium salt, or effervescent mixtures; and/or f) absorbents, colorants, flavors and sweeteners.

Tablets may be either film coated or enteric coated according to methods known in the art.

Preferably, the compound or composition is prepared for oral administration, such as a tablet or capsule, for example, and optionally packaged in a multi-dose format suitable for storing and/or dispensing unit doses of a pharmaceutical product. Examples of suitable packaging include, but are not limited to, hermetically sealed foils, unit dose containers (e.g., vials), blister packs, and strip packs.

Tablets may contain the active ingredient in admixture with nontoxic, pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In some embodiments, the therapeutically effective amount of a crystalline form of a compound of Formula (I) is between about 150 mg per day, and about 2000 mg per day. In particular embodiments, the effective amount is between about 150 mg per day and about 300 mg per day. The dosage may be administered in 1-4 doses per day, or it may be administered on alternating days or with multiple days passing between administrations. In a preferred embodiment, the dosage is about 1000 mg per day, and is administered in one or two oral doses per day.

Unless otherwise specified, the weight or dosage referred to herein for a particular compound (e.g., a compound of Formula (I)) or crystalline form thereof of the disclosure is the weight or dosage of the compound itself, not that of a salt or solvate thereof, which can be different to achieve the intended therapeutic effect. For example, the weight of a corresponding salt of a compound suitable for the methods, compositions, or combinations disclosed herein may be calculated based on the ratio of the molecular weights of the salt and compound itself.

The crystalline forms of 4-(2-((1R,2R)-2-hydroxycyclohexylamino)benzothiazol-6-yloxy)-N-methylpicolinamide described herein are also useful as active pharmaceutical ingredients (APIs) as well as materials for preparing formulations that incorporate one or more pharmaceutically acceptable excipients and are suitable for administration to human subjects. In some embodiments these formulations will be a pharmaceutical product, such as, for example, a solid oral dosage form such as tablets and/or capsules. In the preparation of these formulations it may be the case that the crystalline form of 4-(2-((1R,2R)-2-hydroxycyclohexylamino)benzothiazol-6-yloxy)-N-methylpicolinamide is not detectable in any sufficient amount. Such is the case where a crystalline API is contacted with one or more pharmaceutically acceptable excipients in the presence of a solvent such as, for example, water, in an amount sufficient to promote dissolution of the API such that its crystalline character is lost and therefore is absent in the final pharmaceutical product.

As used herein, the term "pharmaceutically acceptable excipients" includes any and all solvents, carriers, diluents, dispersion media, coatings, surfactants, antioxidants, preservatives (e.g., antibacterial agents, antifungal agents, antioxidants), isotonic agents, absorption delaying agents, salts, drug stabilizers, binders, additives, bulking agents, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). It should be understood that unless a conventional excipient is incompatible with the active ingredient, the use of any conventional excipient in any therapeutic or pharmaceutical compositions is contemplated by the present application.

Accordingly, in an embodiment of the disclosure, a crystalline form of a dihydrochloride monohydrate salt of 4-(2-((1R,2R)-2-hydroxycyclohexylamino)benzothiazol-6-yloxy)-N-methylpicolinamide (Form A) is provided in a substantially phase pure form. This crystalline form of a dihydrochloride monohydrate salt of 4-(2-((1R,2R)-2-hydroxycyclohexylamino)benzothiazol-6-yloxy)-N-methylpicolinamide (Form A) in substantially phase pure form may be used to prepare pharmaceutical compositions which may further comprising one or more pharmaceutically acceptable excipients. In some embodiments the dihydrochloride monohydrate salt of 4-(2-((1R,2R)-2-hydroxycyclohexylamino)benzothiazol-6-yloxy)-N-methylpicolinamide may not retain its crystallinity in the pharmaceutical composition. For example, in some embodiments crystalline Form A may be used in a process to prepare a pharmaceutical composition that, for example, involves spray drying or wet granulation; thus it is expected that little to no crystalline Form A will be detected in the resulting pharmaceutical composition. It should be understood that the term "contacting" as used herein expressly includes methods of combining the crystalline forms of the compound of Formula I described herein where the crystallinity of the API is maintained or the crystallinity of the API is lost as a result of the process of preparing the pharmaceutical composition or pharmaceutical product.

In one embodiment, a composition is provided comprising crystalline Form A together with Form B. In another embodiment, a composition is provided comprising crystalline Form A together with an amorphous form of 4-(2-((1R,2R)-2-hydroxycyclohexylamino)benzothiazol-6-yloxy)-N-methylpicolinamide. In some embodiments the amorphous form is a non-salt (free base) of 4-(2-((1R,2R)-2-hydroxycyclohexylamino)benzothiazol-6-yloxy)-N-methylpicolinamide The crystalline di-hydrochloride monohydrate salt of 4-(2-((1R,2R)-2-hydroxycyclohexylamino)benzothiazol-6-yloxy)-N-methylpicolinamide (Form A) exists primarily as a crystalline material. Form A is hygroscopic, having a maximum water uptake of about 10.79% at 25° C. and up to 95% relative humidity (RH)). In general, Form A shows little to no phase change on exposure to humidity. Form A has a very low aqueous solubility at neutral pH (about 0.006 mg/mL), however it has a high aqueous solubility at low pH (about >20 mg/mL).

Five hydrated forms of the di-hydrochloride salt were identified, which included the crystalline di-hydrochloride monohydrate salt of 4-(2-((1R,2R)-2-hydroxycyclohexylamino)benzothiazol-6-yloxy)-N-methylpicolinamide (Form A) discussed herein. Among the different hydrates identified, crystalline Form A is the more thermodynamically stable hydrate as compared to the other four hydrated forms at ambient conditions. Moreover, Form A was shown to have better physical and chemical stability properties as compared to the other hydrated forms identified. In particular, Form A was shown to be physically and chemically stable in bulk when exposed for one week at 80° C. at ambient relative humidity. Specifically, analysis of the crystalline Form A drug substance indicated that there was less than 1% degradation of the Form A material under these conditions. Form A also proved to be physically and chemically stable in bulk for one to two weeks at 50° C. at ambient relative humidity as well as at 50° C. at 75% relative humidity. Specifically, analysis of the crystalline Form A drug substance indicated that there was less than 1% degradation of the Form A material under both sets of conditions.

Other solvated forms of the di-hydrochloride salt of 4-(2-((1R,2R)-2-hydroxycyclohexylamino)benzothiazol-6-yloxy)-N-methylpicolinamide were also identified, namely, an ethanol solvate as well as a 2-propanol solvate.

It was also found that the intrinsic dissolution rate of the di-hydrochloride monohydrate salt (Form A) is about 150 fold greater than that of the mono-hydrochloride salt (Form B) at pH 4.5.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. Exemplary methods of preparing the crystalline forms described herein are set forth in detail below.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvents, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature. This may also be referred to as a suspension.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Alternatively, crystalline forms may be prepared directly from the reaction medium of the final process for preparing 4-(2-((1R,2R)-2-hydroxycyclohexylamino)benzothiazol-6-yloxy)-N-methylpicolinamide. This may be achieved, for example, by employing in the final process step a solvent or a mixture of solvents from which hydrochloride salts of 4-(2-((1R,2R)-2-hydroxycyclohexylamino)benzothiazol-6-yloxy)-N-methylpicolinamide may be crystallized. In addition, crystalline forms may be obtained by distillation or solvent addition techniques.

In addition to the methods discussed briefly below, it should be understood that various analytical methods may be used for the characterization of any of the materials described herein.

In a different aspect of the present disclosure, crystalline Form A may be characterized by an X-ray powder diffraction pattern (XRPD) comprising 2θ values (CuKα λ=1.5418 Å) comprising a representative peak, in terms of °2θ, at 12.1±0.2 °2θ, measured at a temperature of about 22° C. In another embodiment, the XRPD pattern further comprises one or more additional representative peaks chosen from 7.3±0.2 °2θ, 10.9±0.2 °2θ, and 17.9±0.2 °2θ. Accordingly, the XRPD pattern for the crystalline form of the di-hydrochloride monohydrate salt of the compound of Formula I may comprise one, two, three, or four representative peaks. In another embodiment, the crystalline form of the di-hydrochloride monohydrate salt of the compound of Formula I has an XRPD pattern that may further include one or more additional representative peaks chosen from 8.9±0.2 °2θ and 24.2±0.2 °2θ. Thus, the XRPD pattern for the crystalline form of the di-hydrochloride monohydrate salt of the compound of Formula I may comprise one, two, three, four, five or six representative peaks, measured at a temperature of about 22° C. and an X-ray wavelength, λ, of 1.5418 Å. Specifically, in one embodiment, crystalline Form A may be characterized by a powder X-ray diffraction pattern comprising a peak at 12.1±0.2 °2θ(CuKα λ=1.5418 Å) and one or more peaks chosen from, 7.3±0.2 °2θ, 8.9±0.2 °2θ, 10.9±0.2 °2θ, 17.9±0.2 °2θ and 24.2±0.2 °2θ, measured at a temperature of about 22° C.

Unless otherwise indicated, the terms "a" and "an" are taken to mean "one", "at least one" or "one or more". Unless otherwise required by context, singular terms used herein shall include pluralities and plural terms shall include the singular. For clarity, the contents of any patents, patent applications, and references cited throughout this specification are hereby incorporated by reference in their entireties.

The following non-limiting examples are illustrative of the disclosure.

EXAMPLES

The various crystalline forms of 4-(2-((1R,2R)-2-hydroxycyclohexylamino)benzothiazol-6-yloxy)-N-methylpicolinamide described herein were prepared as follows. It should be understood that these examples are illustrative and that these materials may be prepared according to other methods described herein or via methods known in the art.

(Form A) Di-Hydrochloride Monohydrate Salt of 4-(2-((1R,2R)-2-hydroxycyclohexylamino)benzothiazol-6-yloxy)-N-methylpicolinamide To a clear solution of 4-(2-((1R,2R)-2-hydroxycyclohexylamino)benzothiazol-6-yloxy)-N-methylpicolinamide free base in THF at 60-65° C. was added 6N HCl in H$_2$O (3.0 equivalents). The reaction mixture was stirred at 60-65° C. for about 6 hours. The resulting solids were filtered, washed with fresh THF and dried to yield crystalline Form A.

Ethanol Solvate of Di-Hydrochloride Salt of 4-(2-((1R,2R)-2-hydroxycyclohexylamino)benzothiazol-6-yloxy)-N-methylpicolinamide Approximately 10 mg of di-hydrochloride monohydrate salt of 4-(2-((1R,2R)-2-hydroxycyclohexylamino)benzothiazol-6-yloxy)-N-methylpicolinamide was stirred in neat ethanol at 25° C. for about 24 hrs. The suspension was then filtered and the resulting solids air-dried. XRPD analysis of the recovered material indicated a highly crystalline ethanol solvate was formed.

Approximately 10 mg of di-hydrochloride monohydrate salt of 4-(2-((1R,2R)-2-hydroxycyclohexylamino)benzothiazol-6-yloxy)-N-methylpicolinamide was stirred in a 94% ethanol in water solution at 25° C. for about 24 hrs. The suspension was then filtered and the resulting solids air-dried. XRPD analysis of the recovered material indicated the presence of the same ethanol solvate produced via equilibration with neat ethanol.

2-Propanol Solvate of Di-Hydrochloride Salt of 4-(2-((1R,2R)-2-hydroxycyclohexylamino)benzothiazol-6-yloxy)-N-methylpicolinamide To a clear solution of di-Hydrochloride salt of 4-(2-((1R,2R)-2-hydroxycyclohexylamino)benzothiazol-6-yloxy)-N-methylpicolinamide in 2-propanol was added HCl solution (excess). The resulting solution was allowed to evaporate at ambient temperature. The resulting solids were collected and analyzed by XRPD.

(Form B) Mono-Hydrochloride Salt of 4-(2-((1R,2R)-2-hydroxycyclohexylamino)benzothiazol-6-yloxy)-N-methylpicolinamide To a suspension of 4-(2-((1R,2R)-2-hydroxycyclohexylamino)benzothiazol-6-yloxy)-N-methylpicolinamide free base in isopropyl alcohol (IPA) at 55-60° C. was added HCl in IPA (1.1-1.2 equivalents). The resulting solution was allowed to stir, after which the solution was diluted with isopropyl acetate, concentrated and the solids isolated and analyzed by XRPD.

Powder X-Ray Diffraction

X-ray powder diffraction (XRPD) data were obtained using a Bruker GADDS (General Area Detector Diffraction System) manual chi platform goniometer. Powder samples were prepared between two Kapton foils. The sample-detector distance was 17 cm. The radiation was Cu Kα (λ=1.5418 Å). Data were collected for 3<2θ<40° with a sample exposure time of at least 300 seconds.

TABLE 1

| X-ray powder diffraction data for Form A | | |
|---|---|---|
| Angle | Angle (rounded) | Relative Intensity % |
| 6.273° | 6.3 | 35.4 |
| 7.287° | 7.3 | 76.2 |
| 8.918° | 8.9 | 33.3 |
| 10.891° | 10.9 | 59.7 |
| 12.098° | 12.1 | 97.9 |
| 12.608° | 12.6 | 9.5 |
| 15.481° | 15.5 | 45.4 |
| 15.847° | 15.8 | 17.6 |
| 16.345° | 16.3 | 6.9 |
| 16.763° | 16.8 | 10.8 |
| 17.061° | 17.1 | 19.9 |
| 17.353° | 17.4 | 12.0 |
| 15.847° | 15.8 | 17.6 |
| 16.345° | 16.3 | 6.9 |
| 16.763° | 16.7 | 10.8 |
| 17.061° | 17.1 | 19.9 |
| 17.353° | 17.4 | 12.0 |
| 17.881° | 17.9 | 80.1 |
| 18.458° | 18.4 | 30.5 |
| 19.015° | 19.0 | 100.0 |
| 19.494° | 19.5 | 24.4 |
| 20.222° | 20.2 | 13.4 |
| 20.525° | 20.5 | 26.4 |
| 20.994° | 21.0 | 32.7 |
| 21.294° | 21.2 | 61.7 |
| 21.872° | 21.9 | 42.6 |
| 22.423° | 22.4 | 29.7 |
| 22.692° | 22.7 | 27.7 |
| 23.154° | 23.2 | 18.6 |
| 23.401° | 23.4 | 54.8 |
| 24.185° | 24.2 | 56.6 |
| 24.582° | 24.6 | 14.8 |
| 25.031° | 25.0 | 45.1 |
| 25.399° | 25.4 | 32.3 |
| 25.702° | 25.7 | 51.9 |
| 26.094° | 26.1 | 41.0 |
| 26.581° | 26.6 | 59.8 |
| 27.382° | 27.4 | 60.9 |
| 27.687° | 27.7 | 31.0 |
| 28.489° | 28.5 | 70.9 |
| 29.436° | 29.4 | 44.4 |
| 29.806° | 29.8 | 37.2 |
| 30.205° | 30.2 | 27.4 |
| 30.563° | 30.6 | 45.7 |
| 31.499° | 31.5 | 30.1 |
| 32.179° | 32.2 | 20.9 |
| 33.071° | 33.1 | 23.8 |
| 33.652° | 33.6 | 42.7 |
| 34.528° | 34.5 | 24.5 |
| 35.653° | 35.6 | 18.0 |
| 35.918° | 35.9 | 21.3 |
| 36.316° | 36.3 | 31.9 |
| 36.779° | 36.8 | 30.1 |
| 37.093° | 37.1 | 30.7 |
| 38.204° | 38.2 | 20.1 |
| 38.620° | 38.6 | 23.7 |
| 39.078° | 39.1 | 14.8 |
| 39.498° | 39.5 | 27.2 |

TABLE 2

X-ray powder diffraction data for Form B

| Angle | Angle (rounded) | Relative Intensity % |
|---|---|---|
| 4.2201 | 4.2 | 13.57 |
| 6.4536 | 6.4 | 20.61 |
| 9.7506 | 9.8 | 2.75 |
| 12.3776 | 12.4 | 55.26 |
| 12.8399 | 12.8 | 8.67 |
| 14.4403 | 14.4 | 24.91 |
| 14.5489 | 14.5 | 18.71 |
| 14.9816 | 15.0 | 24.66 |
| 16.6291 | 16.6 | 31.89 |
| 17.9960 | 18.0 | 74.45 |
| 18.0580 | 18.06 | 63.03 |
| 19.4060 | 19.4 | 15.32 |
| 19.9622 | 20.0 | 21.60 |
| 20.8244 | 20.8 | 44.63 |
| 21.1950 | 21.20 | 95.85 |
| 21.2350 | 21.24 | 100.00 |
| 21.2759 | 21.3 | 82.42 |
| 22.1480 | 22.1 | 51.25 |
| 22.2528 | 22.2 | 46.40 |
| 22.6090 | 22.6 | 61.46 |
| 22.6759 | 22.7 | 50.37 |
| 23.7853 | 23.8 | 23.34 |
| 24.7160 | 24.7 | 22.18 |
| 25.7959 | 25.8 | 41.93 |
| 25.8680 | 25.9 | 41.20 |
| 27.0095 | 27.0 | 18.82 |
| 27.8763 | 27.9 | 5.32 |
| 28.2656 | 28.3 | 6.02 |
| 29.0812 | 29.1 | 7.38 |
| 29.3728 | 29.4 | 7.80 |
| 29.9060 | 29.9 | 5.52 |
| 30.7064 | 30.7 | 8.35 |
| 31.3128 | 31.3 | 8.22 |
| 31.7701 | 31.8 | 6.90 |
| 32.1507 | 32.2 | 2.73 |
| 32.8921 | 32.9 | 2.07 |
| 33.8538 | 33.8 | 6.16 |
| 34.7218 | 34.7 | 1.70 |
| 35.4288 | 35.4 | 2.47 |
| 36.7021 | 36.7 | 4.49 |
| 37.9575 | 38.0 | 4.66 |
| 38.8325 | 38.8 | 0.56 |

Thermal Analysis

Crystalline Form A was analyzed using thermogravimetry (TG) and Differential Thermal Analysis (DTA) (Seiko TG/DTA). The cell/sample chamber was purged with 100 ml/min of ultra-high purity nitrogen gas. The instrument was calibrated with high purity indium. The heating rate was 10° C. per minute in the temperature range between 25 and 295° C. with a scan rate of 10 degrees/minute. The heat flow, which was normalized by sample weight, was plotted versus the measured sample temperature. TG data shows % wt loss and energy in micro Volt (uV). The plot was made with the endothermic peaks pointing down. The endothermic melt peak (melting point) was evaluated for extrapolated onset temperature. An illustrative TG/DTA trace generated using crystalline Form A is shown in FIG. 3.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. A crystalline form of a di-hydrochloride monohydrate salt of 4-(2-((1R,2R)-2-hydroxycyclohexylamino)benzothiazol-6-yloxy)-N-methylpicolinamide characterized by an X-ray powder diffraction pattern comprising a peak at 12.1±0.2 °2θ, and one or more peaks chosen from 6.3±0.2 °2θ, 7.3±0.2 °2θ, 10.9±0.2 °2θ, and 17.9±0.2 °2θ, when measured using CuKα radiation with a wavelength of 1.5418 Å and at a temperature of about 22° C., wherein said crystalline form is Form A.

2. The crystalline form according to claim 1 wherein said X-ray powder diffraction pattern comprises one or more peaks chosen from 8.9±0.2 °2θ and 24.2±0.2 °2θ, when measured using CuKα radiation with a wavelength of 1.5418 Å and at a temperature of about 22° C.

3. The crystalline form according to claim 1 wherein said Form A is substantially phase pure.

4. A pharmaceutical composition comprising a crystalline form of a di-hydrochloride monohydrate salt of 4-(2-((1R,2R)-2-hydroxycyclohexylamino)benzothiazol-6-yloxy)-N-methylpicolinamide characterized by an X-ray powder diffraction pattern comprising a peak at 12.1±0.2 °2θ, and one or more peaks chosen from 6.3±0.2 °2θ, 7.3±0.2 °2θ, 10.9±0.2 °2θ, and 17.9±0.2 °2θ, when measured using CuKα radiation with a wavelength of 1.5418 Å and at a temperature of about 22° C., and a pharmaceutically acceptable excipient, wherein said crystalline form is Form A.

5. The pharmaceutical composition according to claim 4 wherein said X-ray powder diffraction pattern comprises one or more peaks chosen from 8.9±0.2 °2θ and 24.2±0.2 °2θ, when measured using CuKα radiation with a wavelength of 1.5418 Å and at a temperature of about 22° C.

6. The pharmaceutical composition according to claim 4 further comprising at least one other solid state form of 4-(2-((1R,2R)-2-hydroxycyclohexylamino)benzothiazol-6-yloxy)-N-methylpicolinamide.

7. The pharmaceutical composition according to claim 4 further comprising the mono-hydrochloride salt of 4-(2-((1R,2R)-2-hydroxycyclohexylamino)benzothiazol-6-yloxy)-N-methylpicolinamide.

8. The pharmaceutical composition according to claim 4 further comprising an amorphous form of 4-(2-((1R,2R)-2-hydroxycyclohexylamino)benzothiazol-6-yloxy)-N-methylpicolinamide or a pharmaceutically acceptable salt thereof.

9. The pharmaceutical composition according to claim 8 wherein the amorphous form is a hydrochloride salt of 4-(2-((1R,2R)-2-hydroxycyclohexylamino)benzothiazol-6-yloxy)-N-methylpicolinamide.

10. The pharmaceutical composition according to claim 4 wherein the Form A is substantially phase pure.

11. A method of treating a glioblastoma multiforme, breast cancer, or pancreatic cancer in a human subject in recognized need of such treatment, said method comprising administering to the human subject a therapeutically effective amount of a crystalline form of a di-hydrochloride monohydrate salt of 4-(2-((1R,2R)-2-hydroxycyclohexylamino)benzothiazol-6-yloxy)-N-methylpicolinamide characterized by an X-ray powder diffraction pattern comprising a peak at 12.1±0.2 °2θ, and one or more peaks chosen from 7.3±0.2 °2θ, 10.9±0.2 °2θ, and 17.9±0.2 °2θ, when measured using CuKα radiation with a wavelength of 1.5418 Å and at a temperature of about 22° C., wherein said crystalline form is Form A.

12. The method according to claim 11 wherein said X-ray powder diffraction pattern comprises one or more peaks chosen from 8.9±0.2 °2θ and 24.2±0.2 °2θ, when measured using CuKα radiation with a wavelength of 1.5418 Å and at a temperature of about 22° C.

13. A method of manufacturing a pharmaceutical composition comprising contacting a crystalline form of a di-hydrochloride monohydrate salt of 4-(2-((1R,2R)-2-hydroxycyclohexylamino)benzothiazol-6-yloxy)-N-methylpicolinamide characterized by an X-ray powder diffraction pattern comprising a peak at 12.1±0.2 °2θ, and one or more peaks chosen from 7.3±0.2 °2θ, 10.9±0.2 °2θ, and 17.9±0.2 °2θ, when measured using CuKα radiation with a wavelength of 1.5418 Å and at a temperature of about 22° C., with at least one pharmaceutically acceptable excipient, wherein said crystalline form is Form A.

14. The method according to claim 13, wherein said Form A is substantially phase pure.

\* \* \* \* \*